United States Patent [19]

Kimball et al.

[11] 4,220,160
[45] Sep. 2, 1980

[54] METHOD AND APPARATUS FOR DISCRIMINATION AND DETECTION OF HEART SOUNDS

[75] Inventors: John P. Kimball; Cesar A. Caceres, both of Washington, D.C.

[73] Assignee: Clinical Systems Associates, Inc., Washington, D.C.

[21] Appl. No.: 922,172

[22] Filed: Jul. 5, 1978

[51] Int. Cl.$^2$ .............................................. A61B 7/04
[52] U.S. Cl. .................................. 128/715; 128/773; 179/1 ST
[58] Field of Search ....................... 128/715, 701, 773; 179/1 ST

[56] References Cited

U.S. PATENT DOCUMENTS

| 3,002,185 | 9/1961 | Bases | 128/715 |
| 3,030,946 | 4/1962 | Richards | 128/715 |
| 3,048,166 | 8/1962 | Rodbard | 128/715 |
| 3,052,756 | 9/1962 | Seven et al. | 128/715 |
| 3,110,770 | 11/1963 | Howell | 128/715 |
| 3,385,937 | 5/1968 | Lafon | 179/107 R |
| 3,562,428 | 2/1971 | Starkey et al. | 179/1 ST |
| 3,895,316 | 7/1975 | Fein | 179/1 ST X |

Primary Examiner—Kyle L. Howell
Attorney, Agent, or Firm—Fleit & Jacobson

[57] ABSTRACT

A method and apparatus for transposition of heart sounds to a range easily detectable by the human ear and suitable for transmission, for discrimination of low intensity or brief sounds, and for display of the heart sounds on conventional recording devices involve steps of and means for, respectively, converting the heart sounds to electrical signals having given frequency components, providing an audio frequency carrier having further frequency components, generating a transposed output representing a sum and a difference of the frequency components and the further frequency components, filtering the transposed output to remove the difference of the frequency components and further frequency components, and generating an audible representation of the heart sounds and/or displaying a visual representation thereof. As a further feature, the inventive method and apparatus provide for detection of an envelope of heart sound intensity, and provision of a visual indication of whether or not electrical signals corresponding to heart sounds are of proper signal amplitude for consistent measurement of heart sound intensity.

14 Claims, 15 Drawing Figures

METHOD AND APPARATUS FOR DISCRIMINATION AND DETECTION OF HEART SOUNDS

BACKGROUND OF INVENTION

1. Field of Invention

This invention relates to medical diagnostic devices and, more particularly, to stethoscopes and electronic signal amplifier systems used to aurally and visually present sounds associated with the heart. This invention is particularly useful for detection and presentation of heart sounds that would be missed by the human ear.

2. Description of Prior Art

The conventional stethoscope presents acoustic information from the heart, some below the usual frequency range of human hearing and some below the sound intensity level of human hearing sensitivity. The conventional loudspeaker and amplifier system approximates the human hearing curve. Such a system will inadequately reproduce whatever low frequency data may be present and will not allow some low sound intensity data that is present to be heard.

Heretofore, various types of schemes have been arranged for frequency modulating (FM) a carrier with heart sounds to produce a signal of higher frequency. These systems present frequencies related to the amplitude of the heart sound, not the frequency. The frequency output of these systems is dependent upon the amplitude of the incoming signal which may be a variable from microphone to microphone. These schemes are typified by relatively inaccurate transposition of heart sound frequency components and poor presentation of low intensity heart sounds, such as murmurs. With FM, the resultant signal is an arbitrary function of the heart sound added to some carrier frequency. The resultant signal will not vary in amplitude, only in frequency. Heterodyne means will not correct this misrepresentation of the human heart sound, nor will demodulation of the FM carrier. FM produces an output frequency that is proportional to the voltage of the heart sound. Moreover, FM produces frequencies related to the heart sound intensity, and not its frequency component content. Data that is present in the heart sound is lost.

Accordingly, there is a substantial need for a device with accuracy as well as sensitivity and such is provided in accordance with the present invention herein.

SUMMARY OF INVENTION

The present invention provides a method and apparatus for transposition of heart sounds, composed of sonic and subsonic frequencies, to a range easily detectable by the human ear and suitable for transmission over conventional phone lines, and for discrimination of low intensity or brief heart sounds, and for display of said heart sounds on conventional visual recording devices, such as: cardiographs, storage type oscilloscopes and chart recorders.

The transposition of said heart sound frequency components involves the addition of a constant frequency component to all of said heart sound frequency components in such a manner as to preserve the spacing between said heart sound frequency components. The transposer circuit achieves said transposition of heart sound frequency components by employing a voltage multiplier of a type for receiving and multiplying said heart sound frequency components with said constant frequency component in such a way as to provide a sum and difference frequency component of said heart sound and constant frequency components (in accordance with suppressed carrier modulation, for example). Said sum and difference frequency components are filtered to produce a sum of said heart sound and constant frequency components. An alternate transposer circuit requiring no filter may be used. Said alternate transposer circuit employs phase shifting networks to shift said heart sound and constant frequency components and multiply and add said phase shifted frequency components with said heart sound and constant frequency components in such a way as to produce a sum of said heart sound frequency components and said constant frequency component.

The sum of all said heart sound frequency components with said constant frequency component is then amplified. The amplified sum may be presented to a conventional loudspeaker, headphone, audio system, phone line, tape recorder, or radio transmitter with suitable bandwidth, for aural interpretation.

The low level heart sound intensity and brief heart sound discriminating circuit achieves said discrimination by employing a full wave rectifier, diode detector and filter to produce an envelope signal that represents the amplitude of the heart sound, although now sharply displayed, continuously in time. Said envelope signal is a voltage which is then compared with manually adjustable threshold voltages. If said envelope signal voltage exceeds said threshold voltages, an output is presented to a suitable display device, such as a cardiograph, indicating to the practitioner that said envelope signal, representing the heart sound amplitude, has exceeded said adjustable threshold levels. This allows the practitioner to detect very low sound intensity levels, as in detection of heart murmurs, or very brief periods of sound, such as 3rd or 4th heart sounds, not generally audible and difficult to display the detection in a manner that is clear and precise. This may allow new diagnostic capabilities to arise.

Said heart sound frequency component transposer and said low level heart sound intensity and brief heart sound discriminator combine to present an improved aural and visual presentation of heart sounds, thus providing the practitioner with a signal containing more heart sound information and of a level more sensitive, accurate and precise than was heretofore possible.

DETAILED DESCRIPTION OF THE INVENTION

Figure 1:
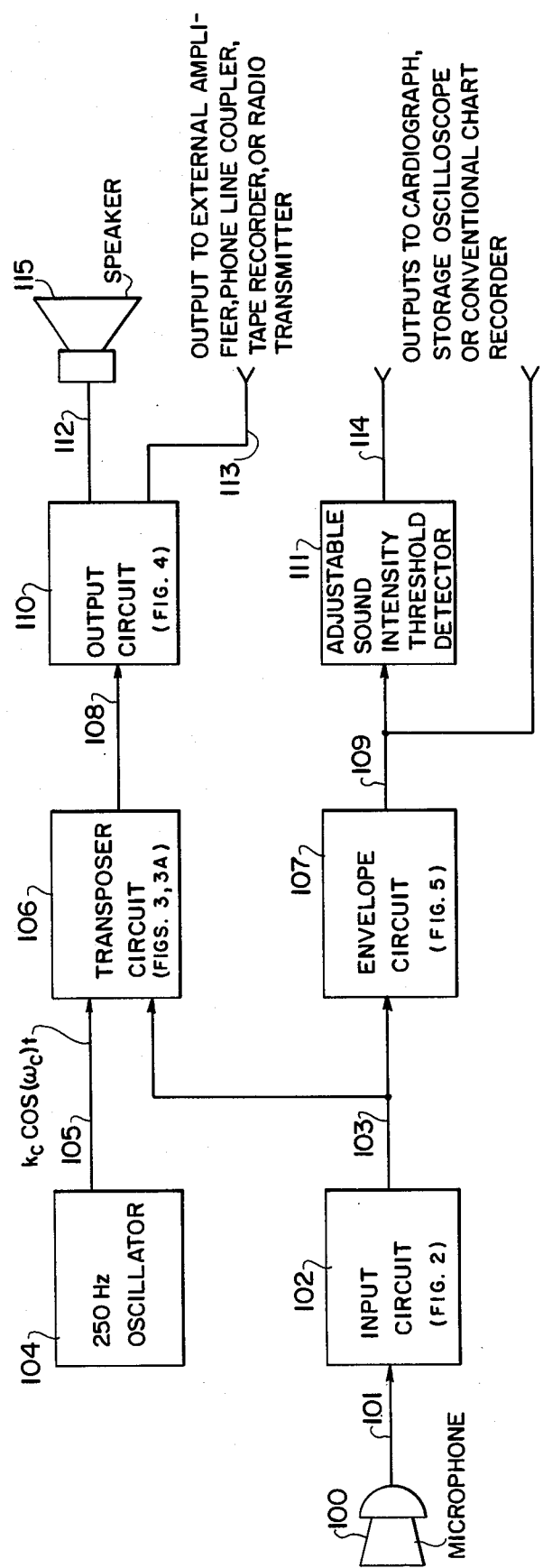
FIG. 1 is a schematic block diagram showing the arrangement of the components of the device constructed in accordance with the present invention.
Figure 2:
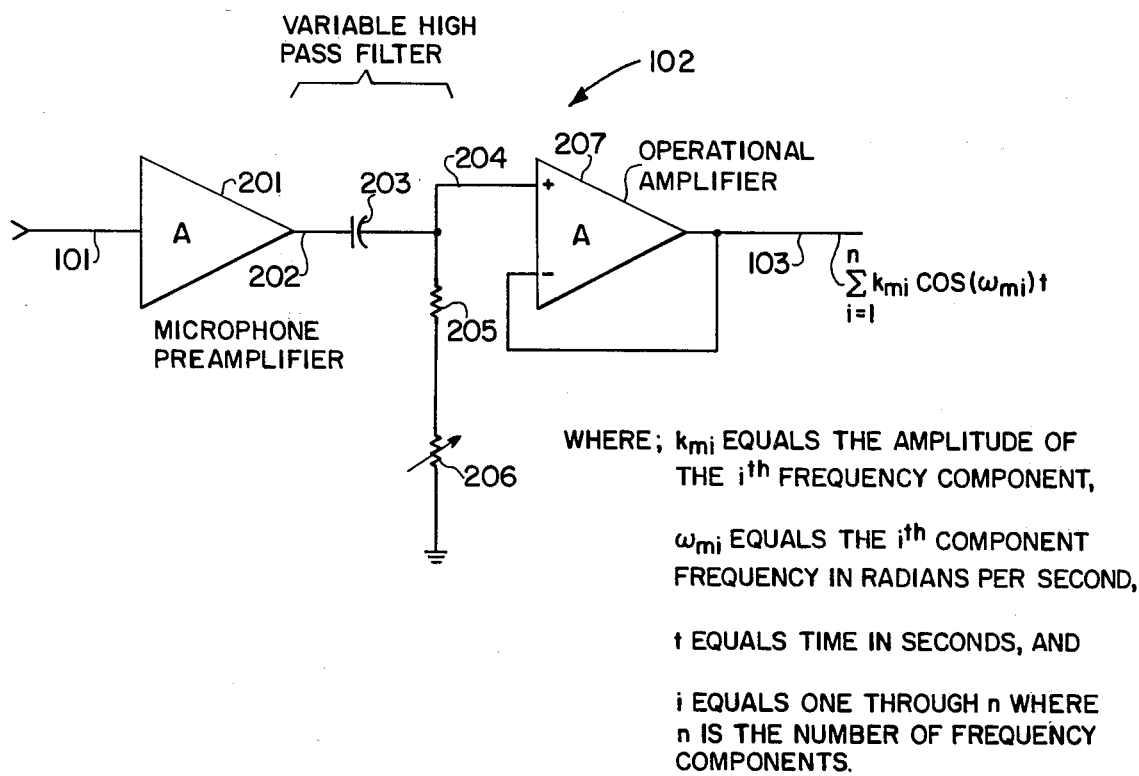
FIG. 2 is a schematic block diagram of the input circuit employed in FIG. 1.
Figure 7G:
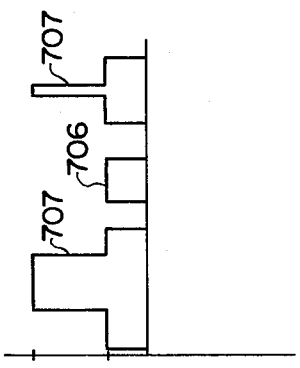
FIGS. 7A–7H are waveform diagrams showing the voltage characteristics (not drawn to scale) at different interconnection points, illustrating operation of the circuits in FIG. 3, FIG. 5 and FIG. 6.
Figure 7H:
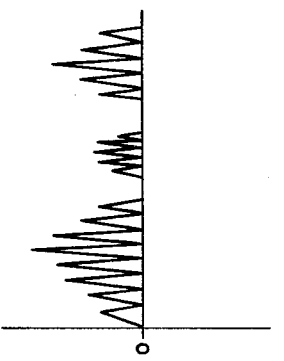
Figure 7D:
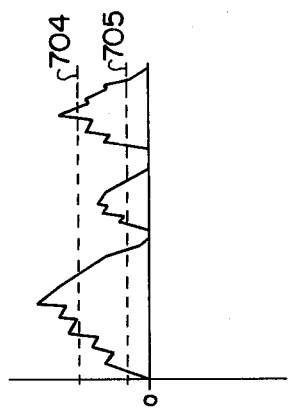
Figure 7E:
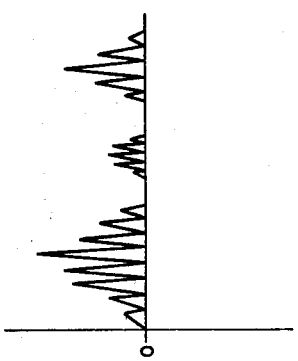
Figure 7F:
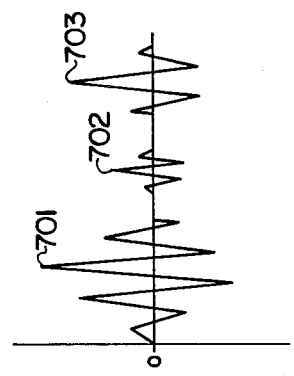
Figure 7A:
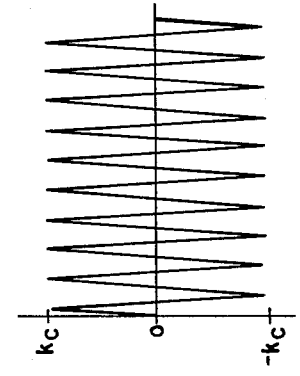
Figure 7B:
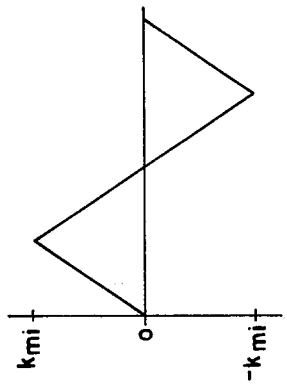

Referring initially to FIG. 1, a conventional microphone for phonocardiographic use is indicated at 100. The output of the microphone is the detected heart sound. The heart sound may have frequency components, generally ranging from DC to 750 Hz. The microphone is connected to the input circuit 102 by means of wire 101. Input circuit 102 is illustrated in FIG. 2. Amplifier 201 amplifies the heart sound signal produced by microphone 100 to a level suitable for processing by apparatus described hereinafter. The output of amplifier 201 is connected to a capacitor 203 via line 202. The capacitor is configured with resistor 205 and variable resistor 206 to form a variable high pass filter. The filter has a cut-off frequency adjustable by variable resistor 206, between 0.5 Hz and 20 Hz. The practitioner may adjust the filter to remove low frequency components of the heart sound. This may facilitate diagnosis of specific murmurs or heart sounds. Amplifier 207 is connected via wire 204 to the filter. Amplifier 207 acts to buffer the filter from circuits described hereinafter. The filtered heart sound from amplifier 207 connects to transposer circuit 106 (FIG. 1) via wire 103. A possible waveform is illustrated in FIG. 7B. A second input to transposer 106 is made from 250 Hz oscillator 104 via wire 105. A typical waveform is illustrated in FIG. 7A. Transposer circuit 106 is illustrated in FIG. 3.

Figure 3:
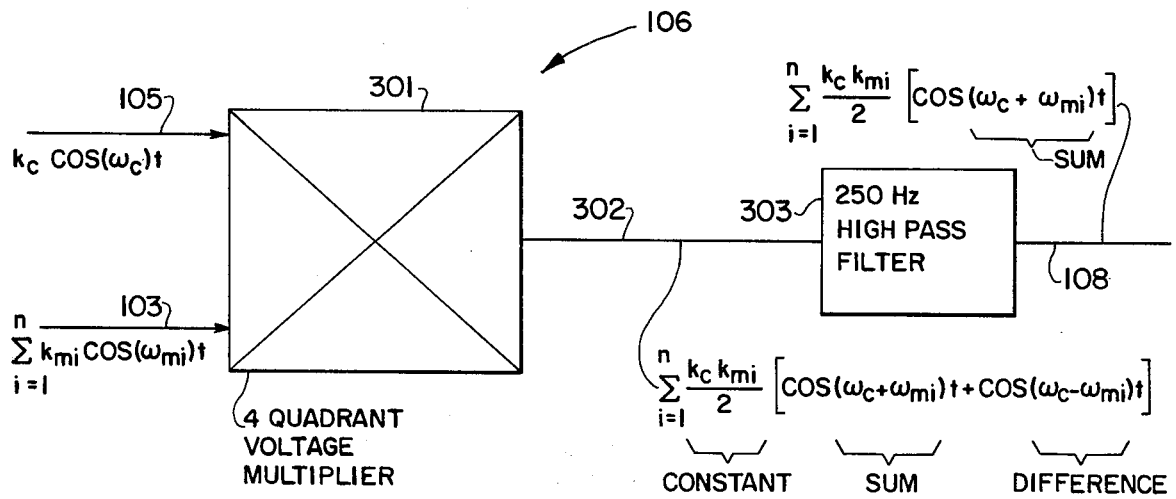
FIG. 3 is a block diagram of the transposer circuit employed in FIG. 1.
Figure 7C:
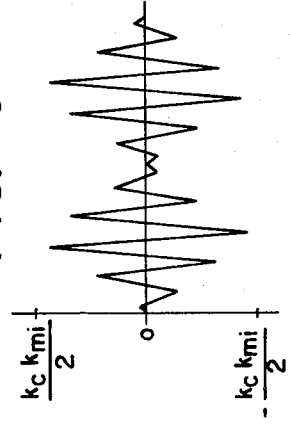

Multiplier 301 of FIG. 3 (included in transposer 106 of FIG. 1) is configured as an amplitude modulator in a balanced mode. A typical multiplier output is shown in FIG. 7C. The multiplier output is a suppressed carrier signal with a sum and difference of the heart sound and oscillator frequency components. It should be apparent that, in a balanced modulator scheme, such as in FIG. 3, any suitable frequency within the human range of hearing may be used in lieu of 250 Hz; however in the application of this invention to heart sound discrimination, a frequency of 250 Hz is recommended. This frequency moves the human heart sound frequency component into the range of 250 Hz to 1000 Hz, an ideal range for the practitioner. In addition, this frequency range is within the constraints of conventional telephone lines. The conventional phone line will pass frequency components between 240 Hz and 1,100 Hz unattenuated. This allows the transmission of a patient's phonocardiogram over conventional phone lines to a practitioner for interpretation.

The output of the multiplier 301 is a sum and difference of the heart sound and 250 Hz oscillator frequency components. This output connects to a 250 Hz high pass filter 303 via wire 302. The filter 303 removes the difference component and the resultant output of filter 303 is a sum of the modulated carrier of 250 Hz with the modulating heart sound. As an example: If the heart sound has frequency components of 25 Hz and 75 Hz, the output of the transposer circuit 106 (FIG. 1) is 250 Hz+25 Hz and 250 Hz+75 Hz, or 275 Hz and 325 Hz. This signal connects to the output circuit 110 via wire 108, illustrated in FIG. 1.

Figure 4:
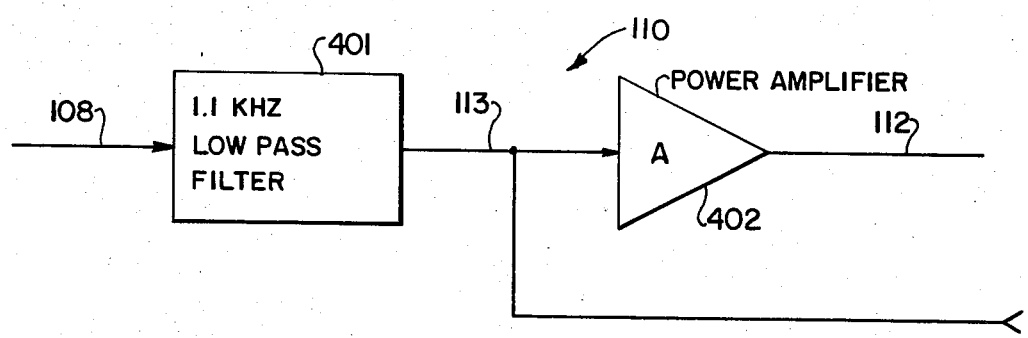
FIG. 4 is a block diagram of the output circuit employed in FIG. 1.

Output circuit 110 is illustrated in FIG. 4. A 1.1 KHz low pass filter 401 receives the signal from filter 303 via wire 108. Filter 401 removes frequencies above 1.1 KHz. Sounds due to breathing are an example. The output of filter 401 is connected to power amplifier 402 via wire 113 and is also available for output to conventional audio devices, such as tape recorders, radio transmitters, headphones and amplifier systems.

Power amplifier 402 is of a conventional design for the purpose of driving a conventional speaker system via wire 112.

The resulting audio signal now has all frequency components present in the heart sound from 0.5 Hz to 750 Hz, transposed to the range of 250.5 Hz to 1000 Hz. The practitioners hearing is, on the average, limited to signals above 30 Hz, and even at 30 Hz the practitioner's sensitivity is low. What was originally below the range of human hearing is now above 250 Hz, by an amount equal to the original value.

Figure 3A:
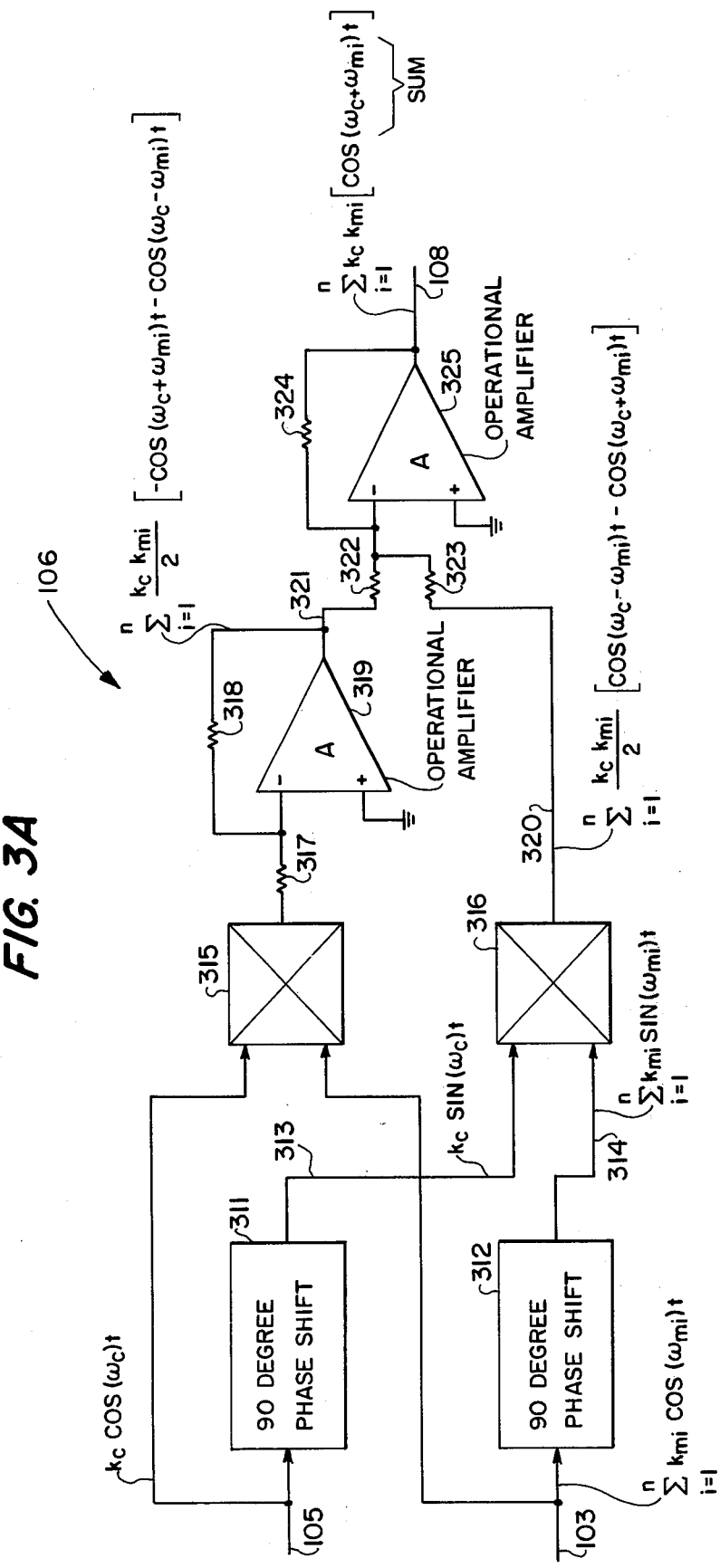
FIG. 3A is a block diagram of an alternate transposer circuit.

The equations relevant to this transposition are illustrated in FIG. 3. The use of a multiplier as a balance modulator has been described by various manufacturers of discrete voltage multipliers, such as Motorola, in linear integrated circuits data book, pp. 8–413, 1973. An alternate technique may be used resulting in inherent suppression of the lower sideband. This circuit is illustrated in FIG. 3A. Ninety degree phase shift circuits 311 and 312 shift the frequency components present in the 250 Hz oscillator and the heart sound signal by 90 degrees, producing appropriate SIN functions. The original 250 Hz carrier is now multiplied with the original heart sound signal by multiplier 315 via wires 105 and 103, respectively. The SIN functions are multiplied together by multiplier 316 via wires 313 and 314. The resultant outputs on wires 321 and 320 represent the negative sum and difference, and the positive difference and negative sum, respectively, as illustrated by equations associated with wires 321 and 320. Amplifier 319 is simply an inverting amplifier acting to change the phase of the signal from multiplier 315 by 180 degrees. Amplifier 325 sums the signals on wires 321 and 320 and the resultant output appears on wire 108. This output on wire 108 is the sum of the 250 Hz carrier frequency component with the heart sound frequency components. This alternate method produces a purer sum than the method illustrated in FIG. 3. A 250 Hz high pass filter, such as filter 303, is not needed to filter out the difference frequencies. However, the method illustrated in FIG. 3A is more complex and an increased number of parts are required to achieve a marginal improvement.

Figure 5:
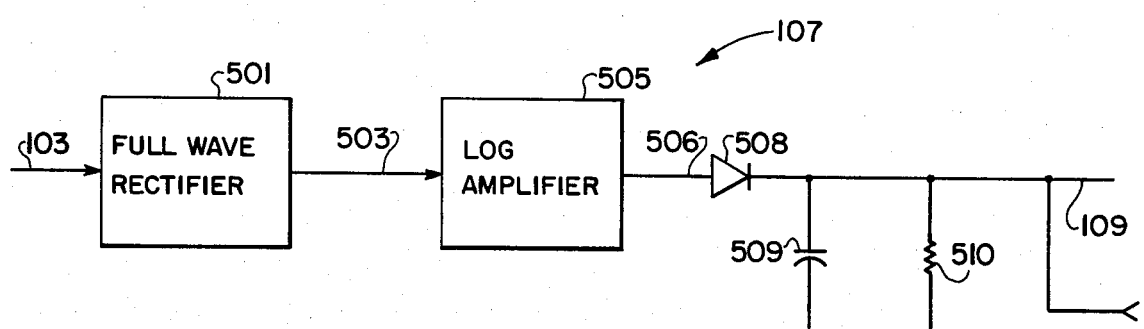
FIG. 5 is a schematic block diagram of the envelope circuit employed in FIG. 1.

To improve the practitioner's ability to discriminate heart sounds, circuits 107 and 111 in FIG. 1 are configured to provide visual display of the heart sound intensity. Circuit 107 is an envelope detector connected to the output of amplifier 207 (FIG. 2) via wire 103. The envelope detector circuit is illustrated in FIG. 5. Full wave rectifier 501 rectifies the heart sound signal. A simplified heart sound waveform is illustrated in FIG. 7D. Waveforms 701 and 703 of FIG. 7D are normal heart sounds and waveform 702 is a low level murmur. The rectified heart sound signal is offset to a level suitable for processing by log amplifier 505 (FIG. 5). The rectified signal waveform is illustrated in FIG. 7E. This signal is provided to log amplifier 505 via wire 503. It is well known that human sensitivity to sound intensity is logarithmic. By amplifying the envelope of the heart sound intensity logarithmically and displaying the resultant signal on a visual recording device, such as a cardiograph, a visual image of heart sound intensity is presented that closely approximates what the practitioner is hearing. A secondary improvement due to amplification by logarithmic means resides in the emphasis placed on low intensity sound. It is well known by those skilled in the art that a log amplifier, such as amplifier 505, will amplify low level signals to a greater degree than high level signals. The log amplified waveform is illustrated in FIG. 7F. The output of log amplifier 505 connects to a diode detector 508 via wire 506. The detected envelope is filtered by capacitor 509 and resistor 510. The detected, filtered output waveform is illustrated in FIG. 7G.

Figure 6:
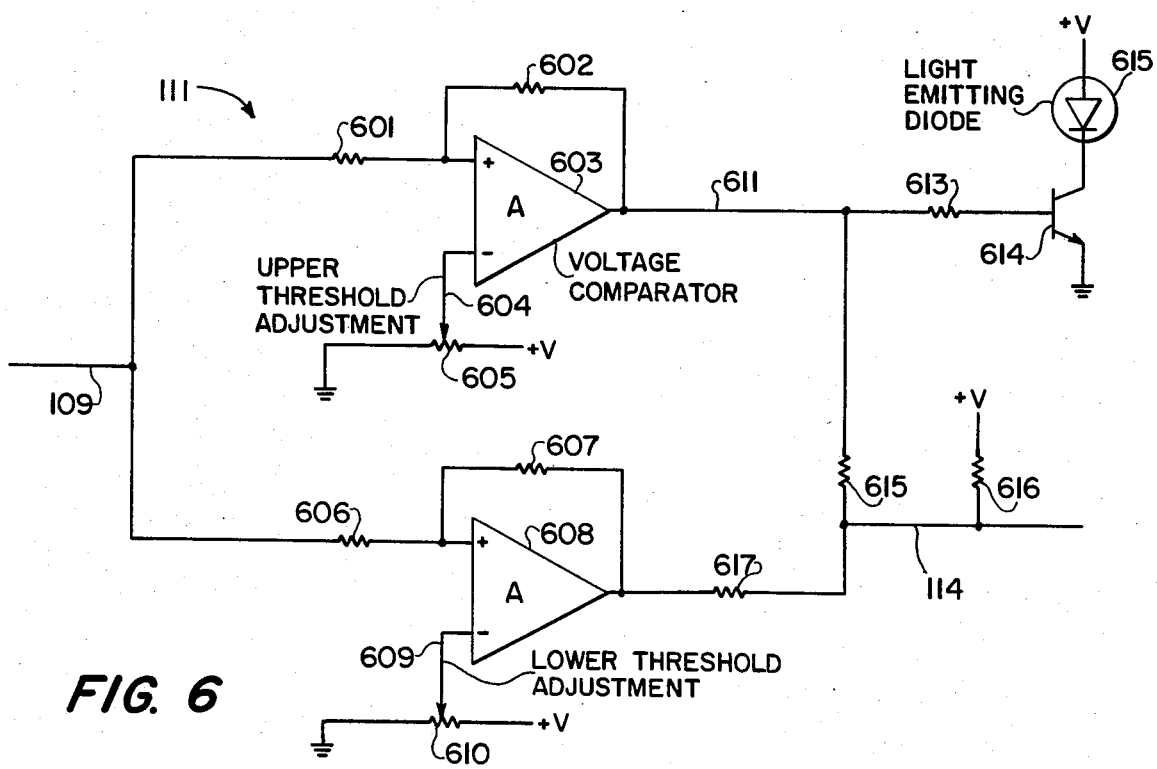
FIG. 6 is a schematic diagram of the adjustable sound threshold detector circuit employed in FIG. 1.

The rectified, amplified, envelope detected and filtered output is connected to the adjustable sound intensity threshold detector 111, illustrated in FIG. 1. FIG. 6 illustrates threshold detector 111 in detail. The detected heart sound intensity envelope signal connects to the adjustable sound intensity threshold detector 111 via wire 109. Amplifier 603 acts as a voltage comparator. The practitioner adjusts variable resistor 605, so that light emitting diode (LED) 615 turns on when an amplitude typical of a first heart sound is detected by amplifier 603. When the heart sound envelope amplitude on wire 109 exceeds the amplitude of the voltage set by the practitioner on wire 604, threshold level 704 of FIG. 7G, the output of amplifier 603 (wire 611) becomes positive, turning on transistor 614. When transistor 614 is on, LED 615 is on. When the heart sound envelope amplitude falls below the amplitude of the voltage set by the practitioner on wire 604, the output of amplifier 603 becomes negative and transistor 614 turns off, as does LED 615. LED 615 indicates to the practitioner the presence of a high intensity heart sound, such as the first and second heart sounds.

Amplifier 608 acts as a voltage comparator and receives the same signal as amplifier 603. The practitioner adjusts the lower threshold variable resistor 610, so that the amplitude at wire 609, as illustrated by voltage level 705 in FIG. 7G, is below the upper threshold variable resistor 605 amplitude at wire 604. An output signal suitable for driving an input of a cardio-graph or chart recorder appears on wire 114. A typical output is illustrated in FIG. 7H. For some low intensity heart sounds, such as murmurs, as illustrated by 702 in FIG. 7D, the heart sound intensity envelope amplitude may only exceed the lower threshold level 705 of FIG. 7G. When this occurs, the configuration of resistors 615, 616 and 617 will produce an output on wire 114 that is a typical voltage of 0.5 volts, as illustrated by 706 in FIG. 7H. If the heart sound intensity envelope amplitude exceeds both the lower and upper thresholds, as in the case of high intensity first and second heart sounds 701 and 703 of FIG. 7D, the output on wire 114 can have a typical voltage of 1.5 volts, as illustrated by 707 in FIG. 7H. This output, when displayed on a chart such as a cardiogram, will provide the practitioner with an indication of a murmur and its relationship in time with normal heart sounds. If the practitioner hears a possible murmur or heart sound using the transposer section of this invention, he may then determine its precise location, relative to the normal heart sounds, or he may use the adjustable sound intensity threshold detector 111 to locate low level heart sounds, such as the third or fourth heart sounds or murmurs, that may be below the human's level of audition.

What is claimed is:

1. Apparatus for improving aural and visual discrimination and detection of heart sounds comprising:
    a transducer means for converting said heart sounds to electrical signals,
    amplifying means connected to said transducer means for amplifying said electrical signals to provide an amplifier output,
    adjustable high pass filter means for receiving and filtering said amplifier output to produce a filtered output having frequency components, wherein said high pass filter means has a cutoff frequency, below which said amplifier output is attenuated and above which said amplifier output is passed,
    oscillator means for providing an audio frequency carrier having frequency components,
    modulator means connected to said adjustable filter means and to said oscillator means for modulating said audio frequency carrier with said filtered output so as to generate a modulator output representing a sum and a difference of said frequency components of said filtered output and said audio frequency carrier,
    high pass filter means connected to said modulator means for filtering said modulator output to produce a further filtered signal representing the sum of said frequency components of said filtered output and said audio frequency carrier, and
    sound intensity discriminating means connected to said adjustable high pass filter means for producing a visual display of said filtered output, whereby to provide visual detection and discrimination of inaudible heart sound events.

2. The apparatus of claim 1 wherein said oscillator means provides an audio frequency carrier having a frequency above 240 Hz, such that sum of the frequency components of said filtered output and said audio frequency carrier is within a frequency range more suitable for transmission over conventional phone lines and for discrimination by a practitioner.

3. The apparatus of claim 1 wherein said modulator means comprises a voltage multiplier.

4. The apparatus of claim 1 wherein said sound intensity discriminating means comprises:
    rectifier means connected to said adjustable high-pass filter means for rectifying said filtered output to produce a rectifier output,
    log amplifier means connected to said rectifier means for logarithmically amplifying said rectifier output so as to provide improved sensitivity to low level heart sounds and producing a log amplifier output,
    a voltage comparator means connected to said log amplifier means for comparing said log amplifier output with adjustable threshold levels to produce a comparison output, and
    display means responsive to said comparison output for providing an indication of proper signal amplitude for consistent measurement of said heart sound intensity levels.

5. The apparatus of claim 4, further comprising visual indicator means responsive to said log amplifier output for producing a visual signal that closely approximates the physiologic hearing intensity curve of the practitioner and amplifies low level sound intensity.

6. The apparatus of claim 1, wherein said adjustable high pass filter means attenuates at least one of unwanted chest movement and unwanted breathing sounds.

7. A method of detecting and discriminating heart sounds utilizing visual and aural display devices, said method comprising the steps of:
    providing said visual device with an upper threshold and a lower threshold potentiometer, frequency transposing said heart sounds to obtain a frequency-transposed heart sound, listening to the frequency-transposed heart sound for heart sounds that may normally be inaudible, adjusting said upper threshold potentiometer for activation of said visual device in the presence of high intensity heart sounds, detecting an envelope of said heart sounds to produce an envelope signal, displaying said envelope signal on said visual device so as to detect low intensity heart sounds, adjusting said lower threshold potentiometer to present a display sharply defining timing between said heart sounds, adjusting said lower threshold potentiometer to visually detect low intensity heart sounds that may normally be inaudible, combining said aural and visual displays of said heart sounds to provide an accurate presentation of said timing, said heart sound intensity, and said frequency of said heart sounds, and visually displaying said envelope of said heart sounds and discriminated sound intensity levels on said visual device.

8. Apparatus for improving aural and visual discrimination and detection of heart sounds, comprising:

input means for receiving and converting said heart sounds to electrical signals having frequency components, oscillator means for providing an audio frequency carrier having further frequency components, transposer means responsive to said electrical signals and to said audio frequency carrier for generating a transposer output including a sum and a difference of said frequency components and said further frequency components, high pass filter means for filtering said transposer output to remove said difference of said frequency components and said further frequency components so as to produce a filtered output, and output means responsive to said filtered output for generating an audible representation of said heart sounds.

9. The apparatus of claim 8, further comprising envelope detecting means responsive to said electrical signals from said input means for detecting an envelope of heart sound intensity therefrom so as to produce an envelope output, and intensity threshold detector means responsive to said envelope output for providing a visual indication having a first state for indicating when said electrical signals are of proper signal amplitude for consistent measurement of said heart sound intensity, and having a second state for indicating when said electrical signals are not of proper signal amplitude for consistent measurement of said heart sound intensity.

10. The apparatus of claim 8, wherein said transposer means comprises means for multiplying said electric signals by said audio frequency carrier.

11. Apparatus for improving aural and visual discrimination and detection of heart sounds, comprising:

input means for receiving and converting said heart sounds to electrical signals having frequency components, oscillator means for providing an audio frequency carrier having further frequency components, transposer means responsive to said electrical signals and to said audio frequency carrier for generating a transposer output including a sum and a difference of said frequency components and said further frequency components, and output means responsive to said filtered output for generating an audible representation of said heart sounds;

said transposing means comprising means for single sideband modulating said audio frequency carrier by said electrical signals to produce an upper sideband output representing a sum of said frequency components.

12. A method of detecting and discriminating heart sounds, comprising the steps of:

receiving and converting said heart sounds to electrical signals, having frequency components, providing an audio frequency carrier having further frequency components, transposing said electrical signals in conjunction with said audio frequency carrier to generate a transposed output including a sum and a difference of said frequency components and said further frequency components, high-pass filtering said transposed output to produce a filtered output, and output processing said filtered output to detect and discriminate said heart sounds.

13. The method of claim 12, wherein said transposing step comprises multiplying said electrical signals by said audio frequency carrier to produce a sum and difference signal.

14. A method of detecting and discriminating heart sounds, comprising the steps of:

receiving and converting said heart sounds to electrical signals, having frequency components, providing an audio frequency carrier having further frequency components, transposing said electrical signals in conjunction with said audio frequency carrier to generate a transposed output, and output processing said transposed output to detect and discriminate said heart sounds;

said transposing step comprising single sideband modulating said audio frequency carrier by said electrical signals to produce an upper sideband output representing a sum of said frequency components.

* * * * *